US012557967B2

(12) United States Patent
Maeda et al.

(10) Patent No.: US 12,557,967 B2
(45) Date of Patent: *Feb. 24, 2026

---

(54) ENDOSCOPIC EXAMINATION SUPPORT APPARATUS, ENDOSCOPIC EXAMINATION SUPPORT METHOD, AND RECORDING MEDIUM

(71) Applicant: NEC Corporation, Tokyo (JP)

(72) Inventors: Naoto Maeda, Tokyo (JP); Takuma Igarashi, Tokyo (JP); Masahiro Saikou, Tokyo (JP); Kimiyasu Takoh, Tokyo (JP); Yuko Maekawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 158 days.

This patent is subject to a terminal disclaimer.

(21) Appl. No.: 18/288,700

(22) PCT Filed: Dec. 5, 2022

(86) PCT No.: PCT/JP2022/044686
§ 371 (c)(1),
(2) Date: Oct. 27, 2023

(87) PCT Pub. No.: WO2024/121886
PCT Pub. Date: Jun. 13, 2024

(65) Prior Publication Data
US 2025/0078348 A1 Mar. 6, 2025

(51) Int. Cl.
*A61B 1/00* (2006.01)
*G06T 7/00* (2017.01)
(Continued)

(52) U.S. Cl.
CPC ...... *A61B 1/000094* (2022.02); *A61B 1/0005* (2013.01); *G06T 7/0012* (2013.01);
(Continued)

(58) Field of Classification Search
CPC . A61B 1/000094; A61B 1/0005; A61B 1/045; G06T 7/0012; G06T 7/66;
(Continued)

(56) References Cited

U.S. PATENT DOCUMENTS

| | | | |
|---|---|---|---|
| 2016/0027174 A1* | 1/2016 | Kang | G06T 11/001 |
| | | | 382/130 |
| 2021/0153720 A1* | 5/2021 | Usuda | A61B 1/07 |

(Continued)

FOREIGN PATENT DOCUMENTS

| | | |
|---|---|---|
| EP | 4095866 A1 | 11/2022 |
| JP | 2012-011109 A | 1/2012 |

(Continued)

OTHER PUBLICATIONS

US Office Action for U.S. Appl. No. 18/530,375, mailed on Jun. 30, 2025.

*Primary Examiner* — Amit Chatly
(74) *Attorney, Agent, or Firm* — Sughrue Mion, PLLC

(57) ABSTRACT

In the endoscopic examination support apparatus, the video acquisition means acquires an endoscopic video captured by an endoscope. The lesion detection means detects a lesion candidate from the endoscopic video. The heat map generation means generates a heat map which represents a lesion possibility of the lesion candidate included in the endoscopic video by a color. The display control means superimposes and displays an area where the lesion possibility is equal to or higher than a first threshold on the endoscopic video in a first display mode, and superimposes and displays an area where the lesion possibility is equal to or higher than a second threshold on the endoscopic video in a second display mode.

5 Claims, 9 Drawing Sheets

(51) Int. Cl.
    G06T 7/66          (2017.01)
    G06T 11/60        (2006.01)
    G16H 30/40      (2018.01)

(52) U.S. Cl.
    CPC ................ G06T 7/66 (2017.01); G06T 11/60
        (2013.01); G16H 30/40 (2018.01); *G06T*
        *2207/10016* (2013.01); *G06T 2207/10024*
        (2013.01); *G06T 2207/10068* (2013.01); *G06T*
        *2207/20081* (2013.01); *G06T 2207/20221*
        (2013.01); *G06T 2207/30096* (2013.01); *G06T*
        *2210/41* (2013.01)

(58) Field of Classification Search
    CPC ........... G06T 11/60; G06T 2207/10016; G06T
        2207/10024; G06T 2207/10068; G06T
        2207/20081; G06T 2207/20221; G06T
        2207/30096; G06T 2210/41; G16H 30/40
    See application file for complete search history.

(56) References Cited

U.S. PATENT DOCUMENTS

| | | | |
|---|---|---|---|
| 2021/0274999 A1* | 9/2021 | Kubota | .............. A61B 1/00045 |
| 2023/0100147 A1* | 3/2023 | Kubota | ............... G06V 10/764 |
| | | | 382/128 |
| 2023/0200626 A1* | 6/2023 | Endo | ....................... G06T 11/00 |
| | | | 345/633 |
| 2024/0029404 A1* | 1/2024 | Watanabe | ........... G06V 10/141 |
| 2024/0180395 A1* | 6/2024 | Maeda | ................... G16H 30/40 |
| 2025/0078348 A1 | 3/2025 | Maeda et al. | |

FOREIGN PATENT DOCUMENTS

| | | |
|---|---|---|
| WO | 2019/138772 A1 | 7/2019 |
| WO | 2019/155628 A1 | 8/2019 |
| WO | 2022/054400 A1 | 3/2022 |

* cited by examiner

<u>100</u>:ENDOSCOPIC EXAMINATION SYSTEM

ENDOSCOPIC EXAMINATION SUPPORT APPARATUS, ENDOSCOPIC EXAMINATION SUPPORT METHOD, AND RECORDING MEDIUM

This application is a National Stage Entry of PCT/JP2022/044686 filed on Dec. 5, 2022, the contents of all of which are incorporated herein by reference, in their entirety.

TECHNICAL FIELD

The present disclosure relates to processing of images relating to an endoscopic examination.

BACKGROUND ART

In the endoscopic examination, there is a technology which detects lesions from endoscopic images and displays the detection result on the endoscopic image. For example, there is a technique to generate a heat map of an endoscopic image including a lesion, and superimpose and display the heat map on the endoscopic image to show the lesion area. Further, Patent Document 1 proposes a method for displaying a frame circumscribing the entire tumor on the endoscopic image at high speed.

PRECEDING TECHNICAL REFERENCES

Patent Document

Patent Document 1: International Publication WO2019/155628

SUMMARY

Problem to be Solved

When a heat map is superimposed on an endoscope image, there is a problem that the original endoscopic image becomes difficult to see. Further, in the method of Patent Document 1, it is impossible to grasp the degree of possibility of the lesion.

One object of the present disclosure is to provide an endoscopic examination support apparatus that can grasp the degree of possibility of the lesion while ensuring the visibility of an endoscopic image.

Means for Solving the Problem

According to an example aspect of the present invention, there is provided an endoscopic examination support apparatus comprising:

a video acquisition means configured to acquire an endoscopic video captured by an endoscope;

a lesion detection means configured to detect a lesion candidate from the endoscopic video;

a heat map generation means configured to generate a heat map which represents a lesion possibility of the lesion candidate included in the endoscopic video by a color; and a display control means configured to superimpose and display an area where the lesion possibility is equal to or higher than a first threshold on the endoscopic video in a first display mode, and superimpose and display an area where the lesion possibility is equal to or higher than a second threshold on the endoscopic video in a second display mode, wherein the second threshold is larger than the first threshold.

According to another example aspect of the present invention, there is provided an endoscopic examination support method comprising:

acquiring an endoscopic video captured by an endoscope;

detecting a lesion candidate from the endoscopic video;

generating a heat map which represents a lesion possibility of the lesion candidate included in the endoscopic video by a color; and superimposing and displaying an area where the lesion possibility is equal to or higher than a first threshold on the endoscopic video in a first display mode, and superimposing and displaying an area where the lesion possibility is equal to or higher than a second threshold on the endoscopic video in a second display mode, wherein the second threshold is larger than the first threshold.

According to still another example aspect of the present invention, there is provided a recording medium recording a program, the program causing a computer to execute:

acquiring an endoscopic video captured by an endoscope;

detecting a lesion candidate from the endoscopic video;

generating a heat map which represents a lesion possibility of the lesion candidate included in the endoscopic video by a color; and superimposing and displaying an area where the lesion possibility is equal to or higher than a first threshold on the endoscopic video in a first display mode, and superimposing and displaying an area where the lesion possibility is equal to or higher than a second threshold on the endoscopic video in a second display mode, wherein the second threshold is larger than the first threshold.

Effect

According to the present disclosure, it is possible to grasp the degree of possibility of the lesion, while ensuring the visibility of the endoscopic video.

EXAMPLE EMBODIMENTS

Preferred example embodiments of the present invention will be described with reference to the accompanying drawings.

First Example Embodiment

[System Configuration]

Figure 1:
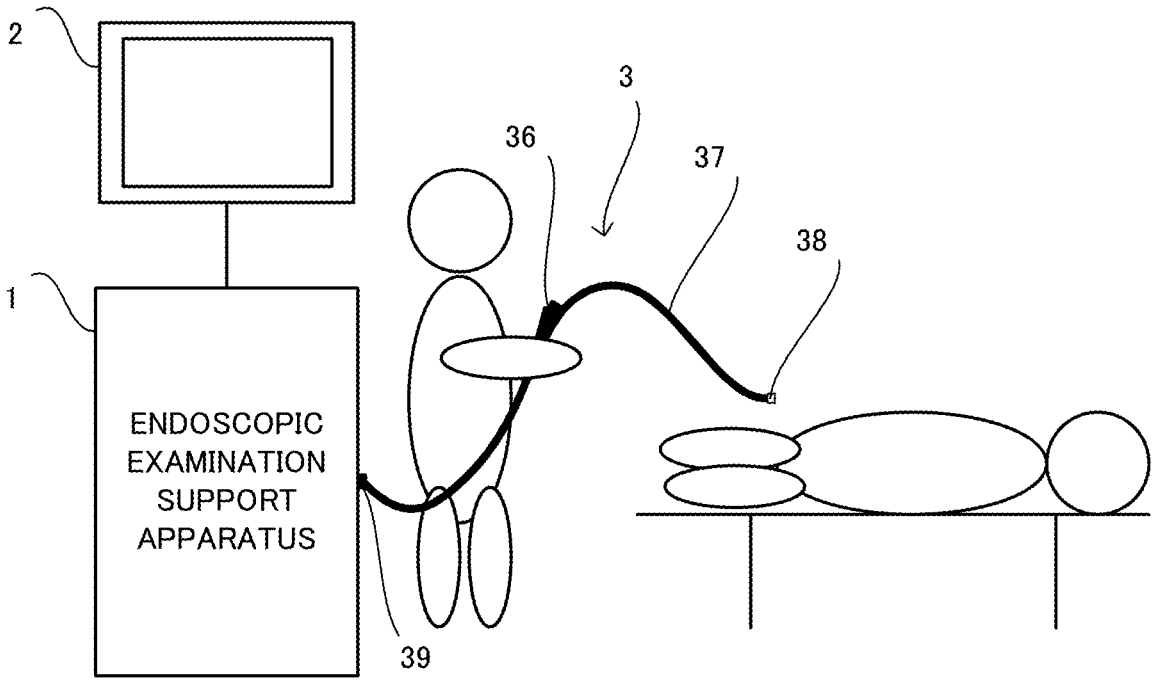
FIG. 1 is a block diagram showing a schematic configuration of an endoscopic examination system.

FIG. 1 shows a schematic configuration of an endoscopic examination system 100. The endoscopic examination system 100 detects a lesion candidate during examination (including treatment) using an endoscope, and displays the detection result of the lesion candidate and the degree of possibility that the lesion candidate is a lesion (hereinafter, referred to as "lesion probability") on an endoscopic video. Thus, a doctor can grasp the lesion candidate and the lesion probability while watching the endoscopic video.

As shown in FIG. 1, the endoscopic examination system 100 mainly includes an endoscopic examination support apparatus 1, a display device 2, and an endoscope 3 connected to the endoscopic examination support apparatus 1.

The endoscopic examination support apparatus 1 acquires a moving image (i.e., a video, hereinafter also referred to as an "endoscopic video Ic") captured by the endoscope 3 during the endoscopic examination from the endoscope 3 and displays the display data for the check by the examiner of the endoscopic examination on the display device 2. Specifically, the endoscopic examination support apparatus 1 acquires a video of the organ captured by the endoscope 3 as an endoscopic video Ic during the endoscopic examination. The endoscopic examination support apparatus 1 extracts frame images from the endoscopic video Ic, and detects lesions using AI (Artificial Intelligence). When the lesion is detected from the frame image by the AI, the endoscopic examination support apparatus 1 generates a heat map based on the frame image. Then, the endoscopic examination support apparatus 1 extracts an area where the lesion probability is highest and an area where the lesion probability is next highest, and superimposes and displays those two areas on the endoscopic video in different manners.

The display device 2 is a display or the like to display an image on the basis of a display signal supplied from the endoscopic examination support apparatus 1.

The endoscope 3 mainly includes an operation unit 36 used by an examiner to input instructions such as air supply, water supply, angle adjustment, and an image-capturing instruction, a shaft 37 having flexibility and inserted into an organ of a subject to be examined, a tip portion 38 with an imaging unit such as an ultra-compact imaging element, and a connection unit 39 for connection with the endoscopic examination support apparatus 1.

[Hardware Configuration]

Figure 2:
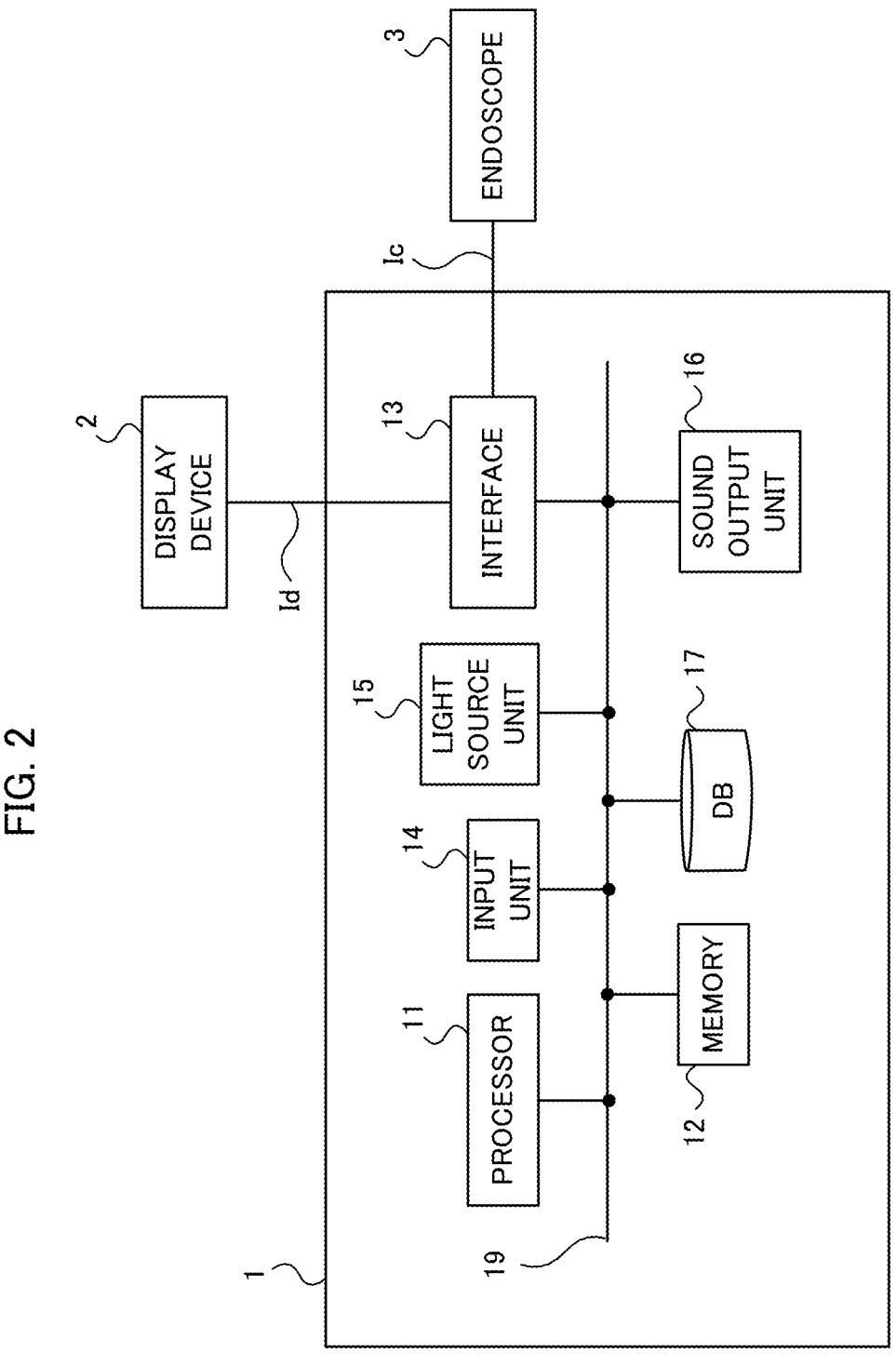
FIG. 2 is a block diagram showing a hardware configuration of an endoscopic examination support apparatus.

FIG. 2 shows a hardware configuration of the endoscopic examination support apparatus 1. The endoscopic examination support apparatus 1 mainly includes a processor 11, a memory 12, an interface 13, an input unit 14, a light source unit 15, a sound output unit 16, and a data base (hereinafter referred to as "DB") 17. Each of these elements is connected via a data bus 19.

The processor 11 executes a predetermined processing by executing a program stored in the memory 12. The processor

11 is a processor such as a CPU (Central Processing Unit), a GPU (Graphics Processing Unit), and a TPU (Tensor Processing Unit). The processor 11 may be configured by a plurality of processors. The processor 11 is an example of a computer.

The memory 12 is configured by various volatile memories used as a working memory and non-volatile memories for storing information needed for processing by the endoscopic examination support apparatus 1, such as a RAM (Random Access Memory) and a ROM (Read Only Memory). Incidentally, the memory 12 may include an external storage device such as a hard disk connected to or incorporated in the endoscopic examination support apparatus 1, and may include a storage medium such as a removable flash memory or a disk medium. The memory 12 stores a program for the endoscopic examination support apparatus 1 to execute each process in the present example embodiment.

Also, the memory 12 temporarily stores a series of endoscopic videos Ic captured by the endoscope 3 during the endoscopic examination, based on the control of the processor 11. Also, the memory 12 temporarily stores the still images acquired from the endoscopic video Ic during the endoscopic examination. These images are stored in the memory 12 in association with information such as an identification information of a subject (e.g., a patient ID) and a time stamp.

The interface 13 performs an interface operation between the endoscopic examination support apparatus 1 and the external devices. For example, the interface 13 supplies the display data Id generated by the processor 11 to the display device 2. Also, the interface 13 supplies the illumination light generated by the light source unit 15 to the endoscope 3. Also, the interface 13 supplies an electrical signal indicating the endoscopic video Ic supplied from the endoscope 3 to the processor 11. The interface 13 may be a communication interface such as a network adapter for wired or wireless communication with an external device, or may be a hardware interface compliant with a USB (Universal Serial Bus), SATA (Serial Advanced Technology Attachment), etc.

The input unit 14 generates an input signal based on the operation of the examiner. The input unit 14 is, for example, a button, a touch panel, a remote controller, a voice input device, or the like. The light source unit 15 generates light to be delivered to the tip portion 38 of the endoscope 3. The light source unit 15 may also incorporate a pump or the like for delivering water or air to be supplied to the endoscope 3. The sound output unit 16 outputs the sound based on the control of the processor 11.

The DB 17 stores the endoscopic images and the lesion information acquired by the previous endoscopic examination of the subject. The lesion information includes a lesion image and associated information. The lesion includes a polyp (protruded lesion). The DB 17 may include an external storage device such as a hard disk connected to or incorporated in the endoscopic examination support apparatus 1, and may include a storage medium such as a removable flash memory. Instead of providing the DB 17 in the endoscopic examination system 100, the DB 17 may be provided in an external server or the like to acquire relevant information from the server through communication.

[Functional Configuration]

Figure 3:
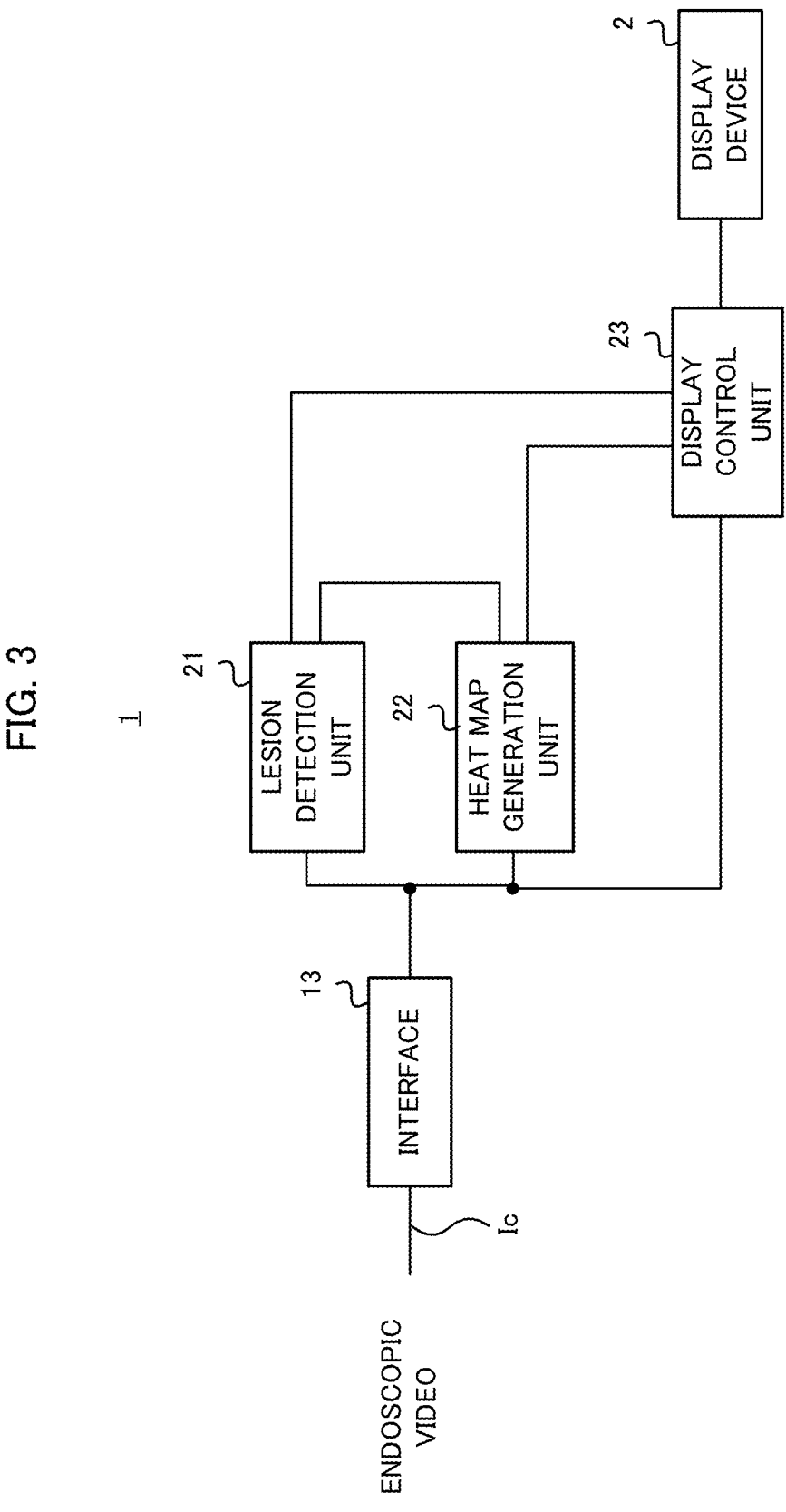
FIG. 3 is a block diagram showing a functional configuration of the endoscopic examination support apparatus.

FIG. 3 is a block diagram showing a functional configuration of the endoscopic examination support apparatus 1. The endoscopic examination support apparatus 1 functionally includes an interface 13, a lesion detection unit 21, a heat map generation unit 22, and a display control unit 23.

To the endoscopic examination support apparatus 1, the endoscopic video Ic is inputted from the endoscope 3. The endoscopic video Ic is inputted to the interface 13. The interface 13 extracts frame images (hereinafter, also referred to as "endoscopic images") from the inputted endoscopic video Ic, and outputs the endoscopic images to the lesion detection unit 21 and the heat map generation unit 22. Further, the interface 13 outputs the inputted endoscopic video Ic to the display control unit 23.

The lesion detection unit 21 performs image analysis on the basis of the endoscopic image inputted from the interface 13 and determines whether or not the lesion is included in the endoscopic image. The lesion detection unit 21 detects a lesion-like portion (hereinafter, also referred to as a "lesion candidate") included in the endoscopic image using an image recognition model prepared in advance. This image recognition model is a model which is learned in advance so as to estimate a lesion candidate included in the endoscopic image, and is also referred to as a "lesion detection model" hereafter. When the lesion candidate is detected, the lesion detection unit 21 outputs the determination result indicating the presence of the lesion to the heat map generation unit 22 and the display control unit 23 together with information such as a time stamp. On the other hand, when the lesion candidate is not detected, the lesion detection unit 21 outputs the determination result indicating the absence of the lesion to the heat map generation unit 22 and the display control unit 23.

The heat map generation unit 22 generates a heat map on the basis of the endoscopic image inputted from the interface 13 and the determination result inputted from the lesion detection unit 21.

Specifically, when the determination result indicating the presence of the lesion is inputted from the lesion detection unit 21, the heat map generation unit 22 acquires the endoscopic image including the lesion candidate from the endoscopic images inputted from the interface 13 on the basis of information such as a time stamp. Then, the heat map generation unit 22 estimates, for each pixel of the endoscopic image, whether or not the pixel is inside the area of the lesion candidate (hereinafter, also referred to as "the lesion area") by using an image recognition model prepared in advance. This image recognition model is a model which is preliminarily learned to estimate whether or not a pixel is in the lesion area for each pixel of the endoscopic image, and is hereinafter also referred to as a "lesion score estimation model".

The heat map generation unit 22 estimates whether or not the pixel is in the lesion area for each pixel of the endoscopic image using the lesion score estimation model, and calculates a score (hereinafter, also referred to as "lesion score") indicating the probability that the pixel is in the lesion area. The lesion score is, for example, a value larger than or equal to 0 and smaller than or equal to 1, and it is likely to be a pixel in the lesion area as the lesion score is closer to 1. Then, the heat map generation unit 22 generates a heat map based on the relationship between the predetermined lesion score and the color. The heat map generation unit 22 outputs the generated heat map to the display control unit 23.

In the above example, the heat map generation unit 22 generates a heat map when the determination result indicating the presence of a lesion is inputted from the lesion detection unit 21. However, the timing of the generating the heat map is not limited to this example. For example, the heat map generation unit 22 may generate a heat map and output it to the display control unit 23, each time the endoscopic image is inputted from the interface 13.

The display control unit 23 generates display data based on the endoscopic video Ic inputted from the interface 13, the determination result inputted from the lesion detection unit 21, and the heat map inputted from the heat map generation unit 22, and outputs the display data to the display device 2.

Specifically, when the determination result indicating the presence of a lesion is inputted from the lesion detection unit 21, the display control unit 23 extracts a predetermined lesion area from the heat map. Then, the display control unit 23 performs a depiction to superimpose the lesion area on the endoscopic video based on the extracted lesion area, and generates the display data. For example, the display control unit 23 compares the lesion score of each pixel of the heat map with a predetermined threshold TH1, and extracts an area formed by the pixels having the lesion score equal to or larger than a threshold TH1 (hereinafter, also referred to as "first threshold area"). Further, the display control unit 23 compares the lesion score of each pixel of the heat map with a predetermined threshold TH2, and extracts an area formed by the pixels having the lesion score equal to or larger than the threshold TH2 (hereinafter, also referred to as "second threshold area"). Then, the display control unit 23 performs a depiction to superimpose the first threshold area and the second threshold area on the endoscope image in different display modes, based on the first threshold area and the second threshold area extracted from the heat map, and generates the display data. Then, the display control unit 23 outputs the display data to the display device 2.

Incidentally, the threshold TH2 is a value larger than the threshold TH1, and the second threshold area indicates the area having the highest probability of lesion. In addition, the first threshold area indicates an area having the second highest probability after the second threshold area. The values of the thresholds TH1 and TH2 can be set for each doctor.

When the determination result indicating the presence of the lesion is inputted from the lesion detection unit 21 continuously a predetermined number of times, the display control unit 23 determines that the lesion candidate is stably detected. Then, the display control unit 23 includes the endoscopic image including the lesion candidate and the heat map in the display data, as the lesion history and the heat map corresponding to the lesion history described later, and outputs the display data to the display device 2. On the other hand, when the determination result indicating the absence of the lesion is inputted from the lesion detection unit 21, the display control unit 23 outputs the endoscopic video Ic to the display device 2 as the display data.

In the above configuration, the interface 13 is an example of a video acquisition means, the lesion detection unit 21 is an example of a lesion detection means, the heat map generation unit 22 is an example of a heat map generation means, and the display control unit 23 is an example of a display control means.

[Display Example]

Next, a display example by the display device 2 will be described.

Figure 4:
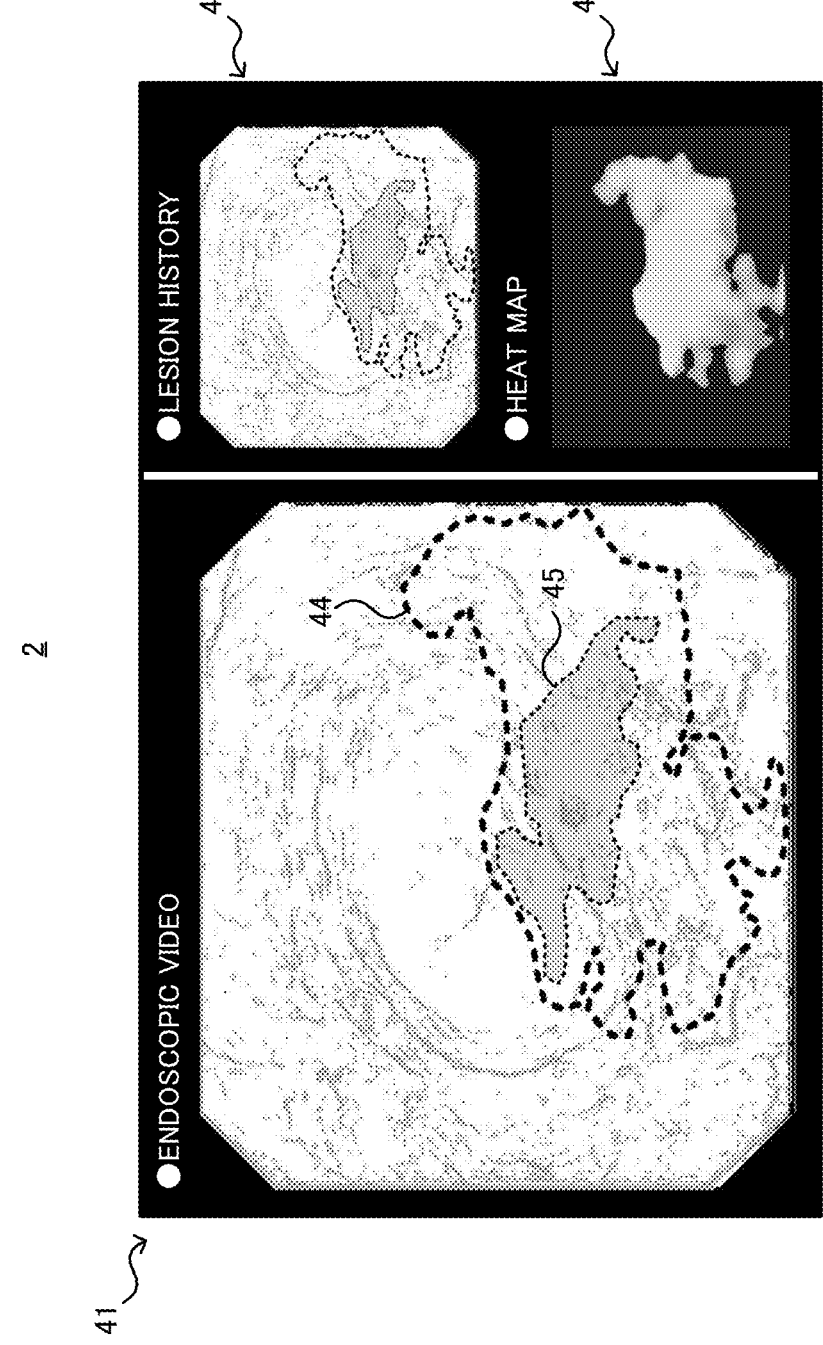
FIG. 4 is a diagram showing a display example of an endoscopic examination support apparatus.

FIG. 4 is a display example by the display device 2. In this example, an endoscopic video 41, a lesion history 42, a heat map 43, a first threshold area 44, and a second threshold area 45 are displayed on the display device 2.

The endoscope video 41 is the endoscopic video Ic during the examination and is updated as the endoscopic camera moves. The lesion history 42 is an endoscopic image that includes a lesion candidate detected during the endoscopic examination. If there are multiple endoscopic images including the lesion candidate, the lesion history 42 displays the endoscopic image including the most recent lesion candidate. The heat map 43 is a heat map of the endoscopic image corresponding to the lesion history 42.

The first threshold area 44 and the second threshold area 45 indicate the lesion areas. Specifically, the first threshold area 44 is an area where the lesion score is equal to or larger than the predetermined threshold TH1. The second threshold area 45 is an area where the lesion score is equal to or larger than the predetermined threshold TH2. The threshold TH2 is larger than the threshold TH1, and the second threshold area 45 indicates the area having the highest lesion probability. Further, different predetermined transparency is set inside the contours of the first threshold area 44 and the second threshold area 45, so that the original endoscopic video is seen through. In FIG. 4, the transparency of the first threshold area 44 is set higher than the transparency of the second threshold area 45. This makes it possible for the doctor to grasp the areas with high lesion probability while monitoring the endoscopic videos.

Figure 5:
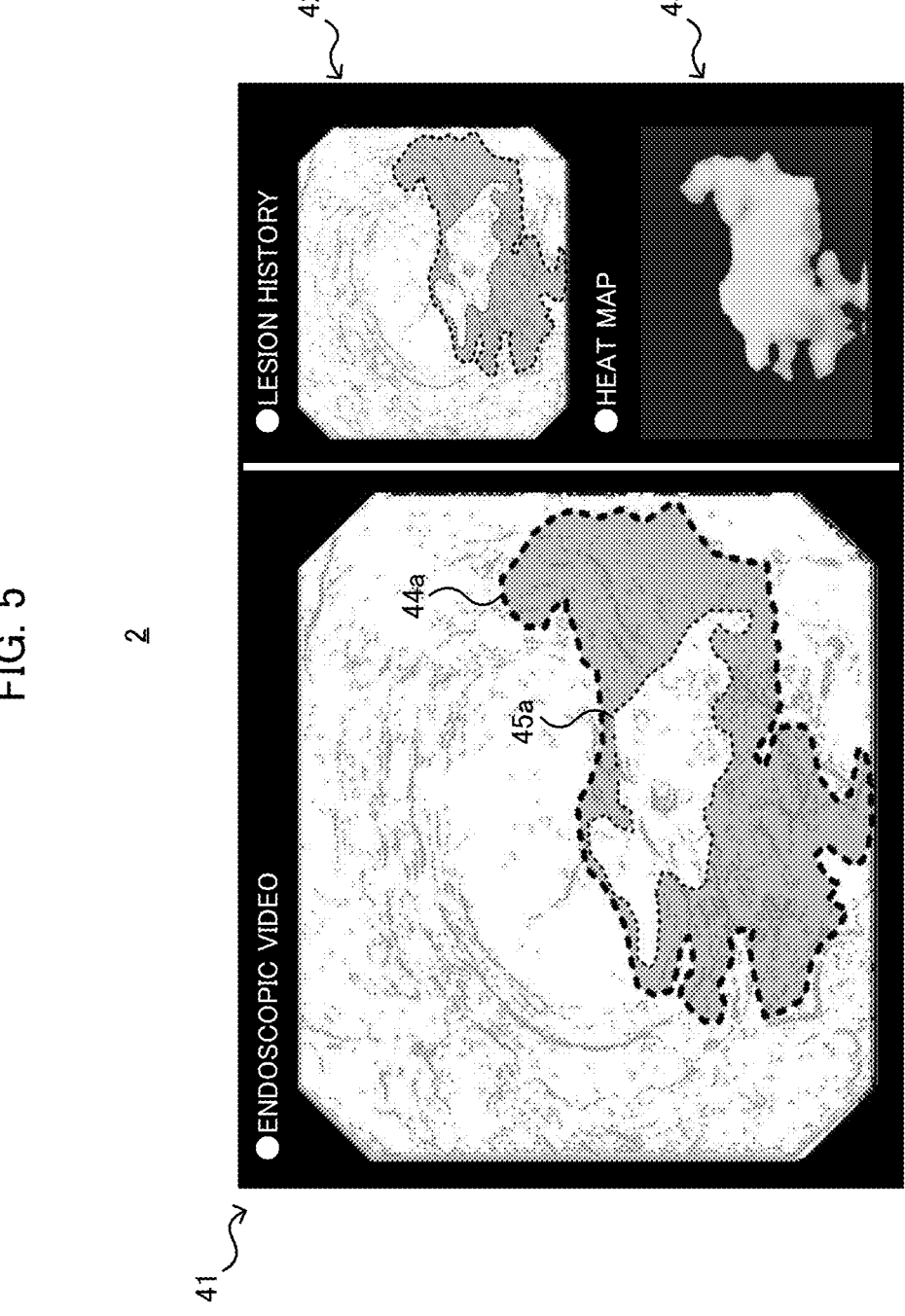
FIG. 5 is a diagram showing another display example of the endoscopic examination support apparatus.

FIG. 5 shows another display example by the display device 2. In FIG. 5, the display mode of the first threshold area and the second threshold area is different from FIG. 4.

The first threshold area 44a is an area where the lesion score is equal to or larger than the predetermined threshold TH1. The second threshold area 45a is an area where the lesion probability is equal to or larger than the predetermined threshold TH2. In FIG. 5, the transparency of the second threshold area 45a is set higher than the transparency of the first threshold area 44a. In the example of FIG. 5, since the second threshold area 45a is inside the first threshold area 44a, the second threshold area 45a is displayed with high transparency, and the area of the first threshold area 44a other than the second threshold area 45a is displayed with low transparency. Thus, in the example of FIG. 5, since the area having high lesion probability is displayed with high transparency, the doctor can easily observe the area where the lesion probability is high.

Figure 6:
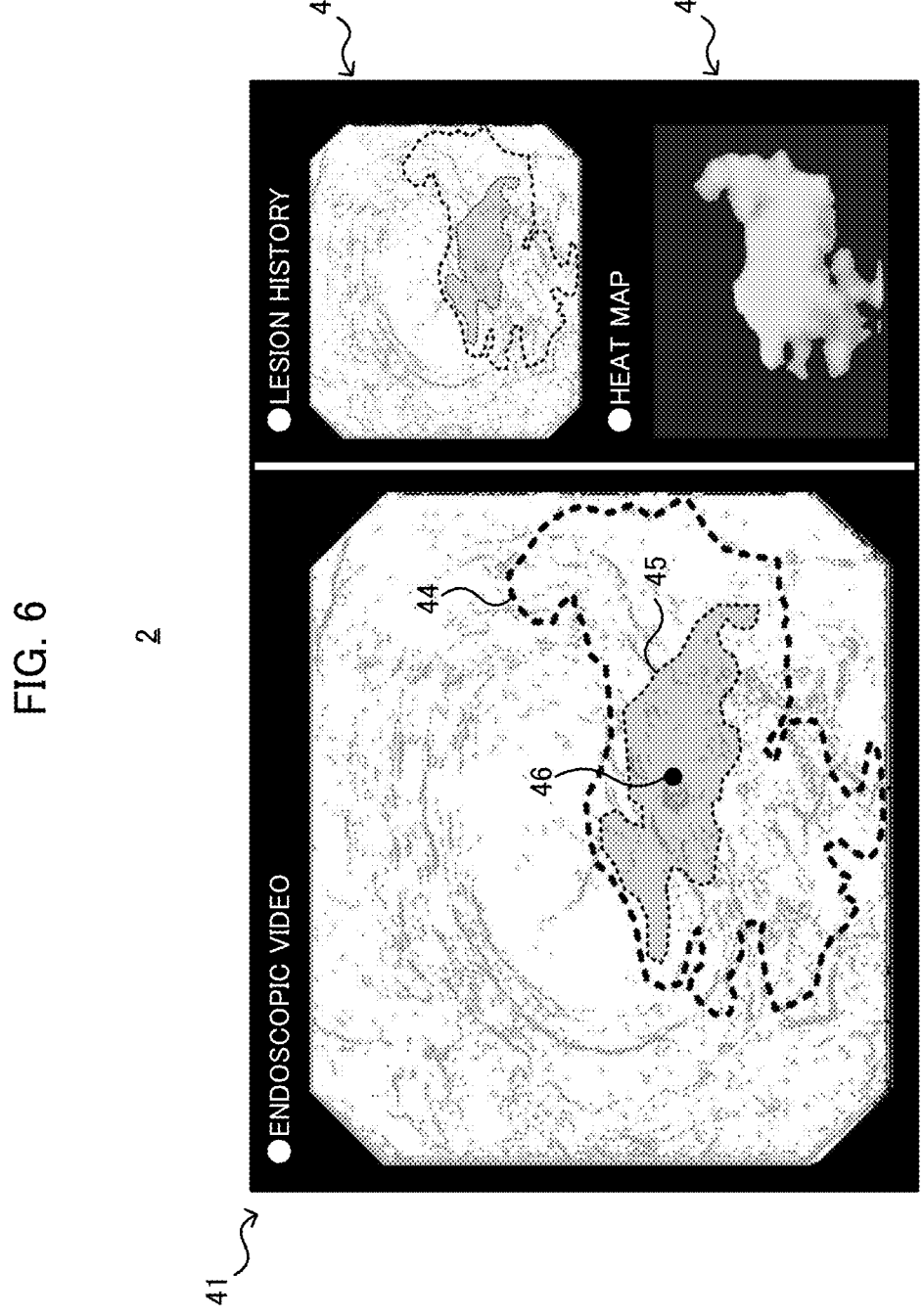
FIG. 6 is a diagram showing still another display example of the endoscopic examination support apparatus.

FIG. 6 shows another display example by the display device 2. In FIG. 6, a center mark 46 is displayed inside the second threshold area 45.

The center mark 46 indicates a suitable position for the collection of specimen. For example, the center mark 46 may be a center position of the circumscribed rectangle of the second threshold area 45, a center position of the inscribed circle of the second threshold area 45, or a center of gravity of the second threshold area 45. The display control unit 23 determines the center position or the center of gravity position as described above based on the second threshold area extracted from the heat map and describes the position with figures or the like on the endoscopic video. By displaying the center mark 46 on the endoscopic video, the doctor can grasp the position suitable for the collection of specimen.

Whether or not to display of the first threshold area 44, the second threshold area 45 and the center mark 46 may be selected by the doctor. The doctor can use the above information in combination freely.

[Image Display Processing]

Figure 7:
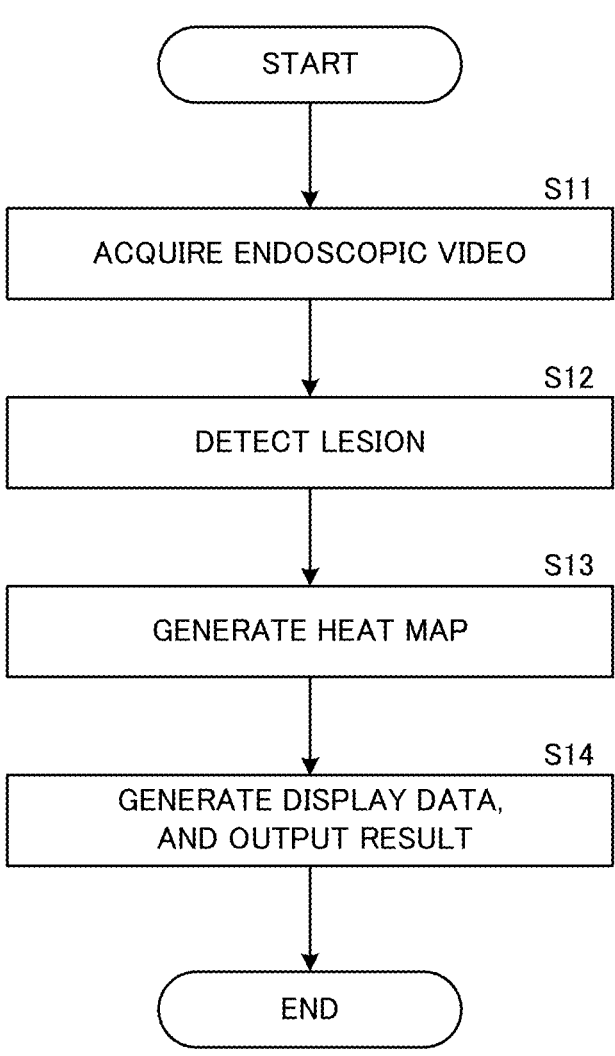
FIG. 7 is a flowchart of display processing by the endoscopic examination support apparatus.

Next, display processing for performing the above-mentioned display will be described. FIG. 7 is a flowchart of processing performed by the endoscopic examination support apparatus 1. This processing is realized by the processor 11 shown in FIG. 2, which executes a pre-prepared program and operates as the elements shown in FIG. 3.

First, an endoscopic video Ic is inputted from the endoscope 3 to the interface 13. The interface 13 acquires endoscopic images from the inputted endoscopic video Ic (step S11). The interface 13 outputs the endoscopic images to the lesion detection unit 21 and the heat map generation unit 22. Also, the interface 13 outputs the endoscopic video Ic to the display control unit 23. Next, the lesion detection unit 21 detects the lesion from the endoscopic images (step S12). Specifically, the lesion detection unit 21 determines whether or not the lesion is included in the endoscopic images by using the lesion detection model. Then, the lesion detection unit 21 outputs the determination result to the heat map generation unit 22 and the display control unit 23.

Next, when the lesion is detected, the heat map generation unit 22 generates a heat map from the endoscopic image (step S13). Specifically, the heat map generation unit 22 estimates the lesion score for each pixel of the endoscopic image using the lesion score estimation model. Then, the heat map generation unit 22 generates a heat map, based on the relationship between the score and the color determined in advance. Then, the heat map generation unit 22 outputs the generated heat map to the display control unit 23.

Next, the display control unit 23 generates display data based on the endoscopic video inputted from the interface 13, the determination result inputted from the lesion detection unit 21, and the heat map inputted from the heat map generation unit 22, and outputs the display data to the display device 2 (step S14). Specifically, when the determination result indicating the presence of the lesion is inputted from the lesion detection unit 21, the display control unit 23 extracts a lesion area from the heat map. Then, the display control unit 23 performs a depiction of superimposing the lesion area on the endoscopic video based on the extracted lesion area, and generates the display data.

Modification

Next, a modification of the first example embodiment will be described. The following modification can be applied to the first example embodiment in appropriate combination.

Modification 1

In the above-described first example embodiment, the display control unit 23 superimposes and displays the first threshold area and the second threshold area on the endoscope image. However, the display control unit 23 may superimpose and display a third threshold area on the endoscope image in addition to the first threshold area and the second threshold area. The display control unit 23 compares the lesion score of each pixel of the heat map with a predetermined threshold TH3, and determines an area formed by the pixels having a lesion score equal to or larger than the threshold TH3 to be the third threshold area. Then, the display control unit 23 performs a depiction of superimposing the first threshold area, the second threshold area, and the third threshold area extracted from the heat map on the endoscope image. By providing the third threshold area, the doctor can perform setting of a more detailed threshold value.

Second Example Embodiment

Figure 8:
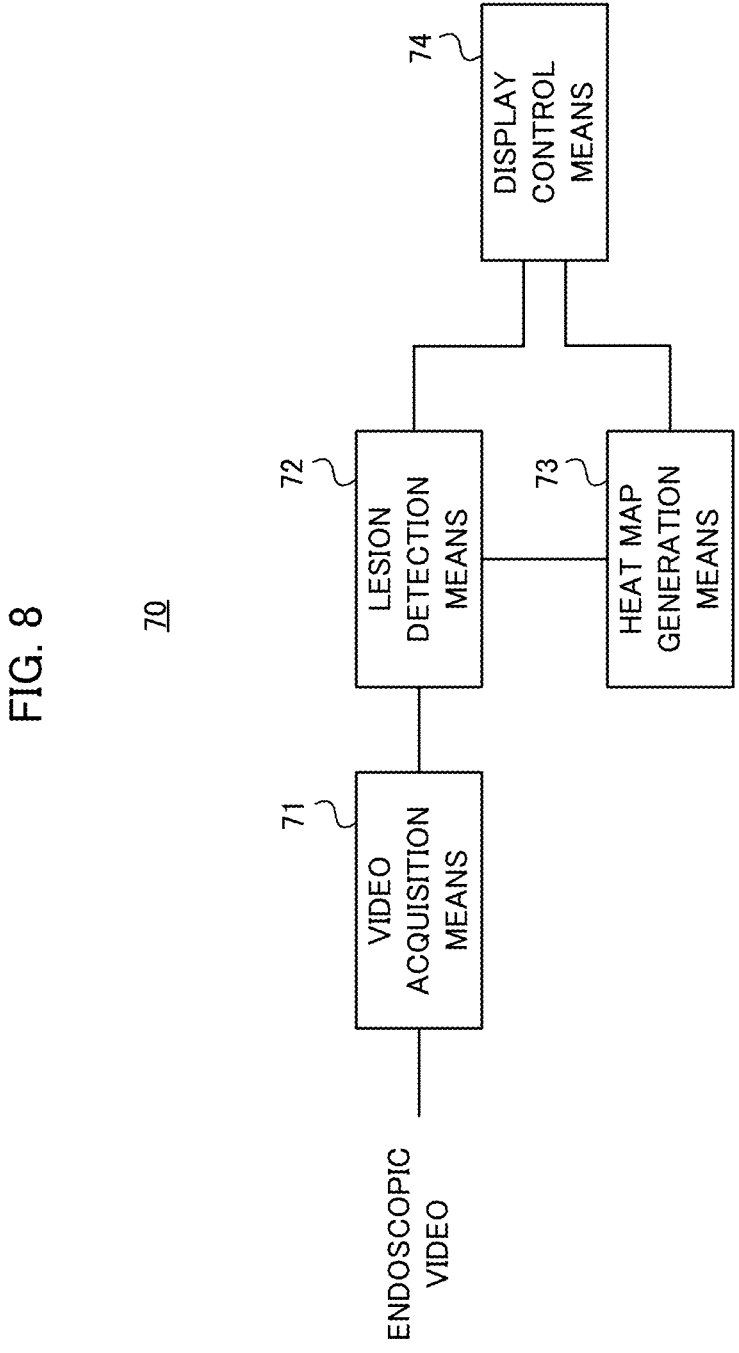
FIG. 8 is a block diagram showing a functional configuration of an endoscopic examination support apparatus of a second example embodiment.

FIG. 8 is a block diagram illustrating a functional configuration of an endoscopic examination support apparatus according to a second example embodiment. The endoscopic examination support apparatus 70 includes a video acquisition means 71, a lesion detection means 72, a heat map generation means 73, and a display control means 74.

Figure 9:
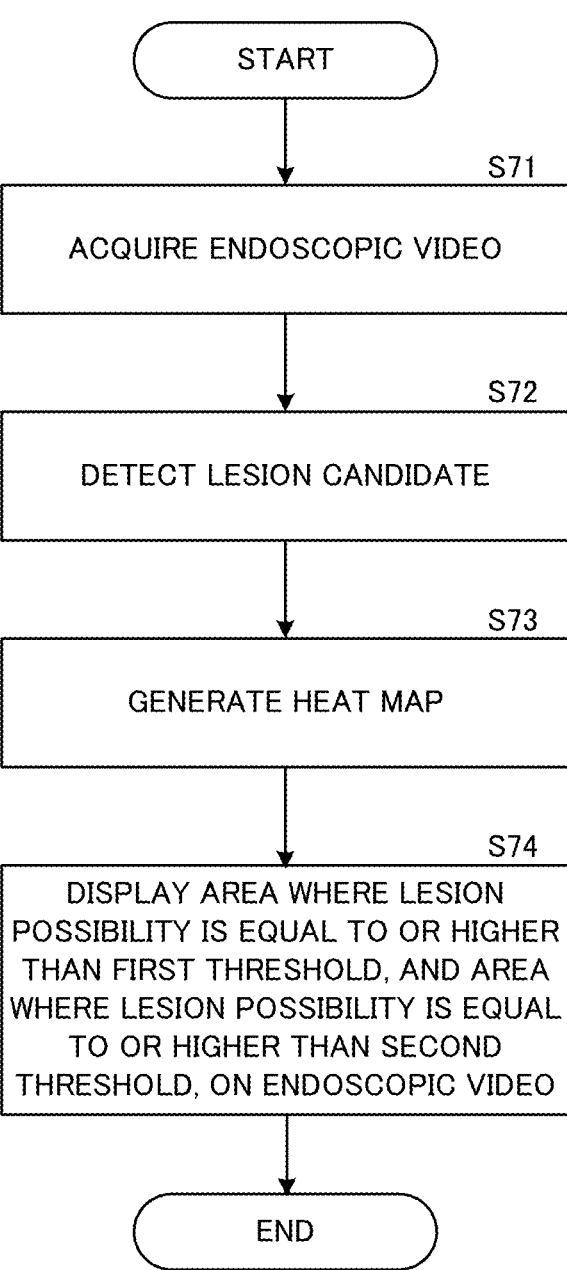
FIG. 9 is a flowchart of processing by the endoscopic examination support apparatus of the second example embodiment.

FIG. 9 is a flowchart of processing performed by the endoscopic examination support apparatus according to the second example embodiment. The video acquisition means 71 acquires an endoscopic video captured by an endoscope (step S71). The lesion detection means 72 detects a lesion candidate from the endoscopic video (step S72). The heat map generation means 73 generates a heat map which represents a lesion possibility of the lesion candidate included in the endoscopic video by a color (step S73). The display control means 74 superimposes and displays an area where the lesion possibility is equal to or higher than a first threshold on the endoscopic video in a first display mode, and superimposes and displays an area where the lesion possibility is equal to or higher than a second threshold on the endoscopic video in a second display mode (step S74).

While the present disclosure has been described with reference to the example embodiments and examples, the present disclosure is not limited to the above example embodiments and examples. Various changes which can be understood by those skilled in the art within the scope of the present disclosure can be made in the configuration and details of the present disclosure.

Supplementary Note 1

An endoscopic examination support apparatus comprising:

a video acquisition means configured to acquire an endoscopic video captured by an endoscope;

a lesion detection means configured to detect a lesion candidate from the endoscopic video;

a heat map generation means configured to generate a heat map which represents a lesion possibility of the lesion candidate included in the endoscopic video by a color; and a display control means configured to superimpose and display an area where the lesion possibility is equal to or higher than a first threshold on the endoscopic video in a first display mode, and superimpose and display an area where the lesion possibility is equal to or higher than a second threshold on the endoscopic video in a second display mode, wherein the second threshold is larger than the first threshold.

Supplementary Note 2

The endoscopic examination support apparatus according to Supplementary note 1, wherein the second display mode is different in transparency from the first display mode.

Supplementary Note 3

The endoscope examination support apparatus according to Supplementary note 2, wherein the second display mode has a higher transparency than the first display mode.

Supplementary Note 4

The endoscopic examination support apparatus according to any one of Supplementary notes 1 to 3, wherein a predetermined mark is superimposed and displayed at a position of a center or a center of gravity of an area having a highest lesion possibility.

Supplementary Note 5

The endoscopic examination support apparatus according to Supplementary note 1, wherein the first threshold and the second threshold are set for each user.

Supplementary Note 6

The endoscopic examination support apparatus according to Supplementary note 4, wherein whether or not to display the first display mode, the second display mode and the predetermined mark is set for each user.

Supplementary Note 7

An endoscopic examination support method comprising:

acquiring an endoscopic video captured by an endoscope;

detecting a lesion candidate from the endoscopic video;

generating a heat map which represents a lesion possibility of the lesion candidate included in the endoscopic video by a color; and superimposing and displaying an area where the lesion possibility is equal to or higher than a first threshold on the endoscopic video in a first display mode, and superimposing and displaying an area where the lesion possibility is equal to or higher than a second threshold on the endoscopic video in a second display mode, wherein the second threshold is larger than the first threshold.

Supplementary Note 8

A recording medium recording a program, the program causing a computer to execute:

acquiring an endoscopic video captured by an endoscope;

detecting a lesion candidate from the endoscopic video;

generating a heat map which represents a lesion possibility of the lesion candidate included in the endoscopic video by a color; and superimposing and displaying an area where the lesion possibility is equal to or higher than a first threshold on the endoscopic video in a first display mode, and superimposing and displaying an area where the lesion possibility is equal to or higher than a second threshold on the endoscopic video in a second display mode, wherein the second threshold is larger than the first threshold.

DESCRIPTION OF SYMBOLS

1 Endoscopic examination support apparatus
2 Display device
3 Endoscope
11 Processor
12 Memory
13 Interface
21 Lesion detection unit
22 Heat map generation unit
23 Display control unit
100 Endoscopic examination system

What is claimed is:

1. An endoscopic examination support apparatus comprising:

a memory configured to store instructions; and a processor configured to execute the instructions to:

acquire an endoscopic video captured by an endoscope;

detect, using a lesion detection model learned in advance, a lesion candidate from the endoscopic video;

generate, using a lesion score estimation model learned in advance, a heat map that represents, for each pixel of an endoscopic image in the endoscopic video, lesion possibilities of the lesion candidate by a color;

extract, from the heat map, a first threshold area formed by pixels whose lesion possibility, of the lesion possibilities, is equal to or greater than a first threshold, and a second threshold area formed by pixels whose lesion possibility, of the lesion possibilities, is equal to or greater than a second threshold larger than the first threshold;

superimpose and display the first threshold area on the endoscopic video in a first display mode and the second threshold area on the endoscopic video in a second display mode, the second display mode having a higher transparency than the first display mode;

superimpose and display, inside the second threshold area, a predetermined mark, at any of a center of the second threshold area and a center of gravity of the second threshold area, as a guide to a position of the lesion candidate; and based on a presence of a lesion being determined to be obtained successively a predetermined number of times from the endoscopic video, determine that the lesion candidate is stably detected and include, in display data of the endoscopic image, an indication of a most recent lesion candidate and the heat map as a lesion history.

2. The endoscopic examination support apparatus according to claim 1, wherein the first threshold and the second threshold are set for each user.

3. The endoscopic examination support apparatus according to claim 1, wherein whether or not to display the first display mode, the second display mode and the predetermined mark is set for each user.

4. An endoscopic examination support method comprising:

acquiring an endoscopic video captured by an endoscope;

detecting, using a lesion detection model learned in advance, a lesion candidate from the endoscopic video;

generating, using a lesion score estimation model learned in advance, a heat map that represents, for each pixel of an endoscopic image in the endoscopic video, lesion possibilities of the lesion candidate by color;

extracting, from the heat map, a first threshold area formed by pixels whose lesion possibility, of the lesion possibilities, is equal to or greater than a first threshold, and a second threshold area formed by pixels whose lesion possibility, of the lesion possibilities, is equal to or greater than a second threshold larger than the first threshold;

superimposing and displaying the first threshold area on the endoscopic video in a first display mode and the second threshold area on the endoscopic video in a second display mode, the second display mode having a higher transparency than the first display mode;

superimposing and displaying, inside the second threshold area, a predetermined mark, at any of a center of the second threshold area and a center of gravity of the second threshold area, as a guide to a position of the lesion candidate; and based on a presence of a lesion being determined to be obtained successively a predetermined number of times from the endoscopic video, determine that the lesion candidate is stably detected and include, in display data of the endoscopic image, an indication of a most recent lesion candidate and the heat map as a lesion history.

5. A non-transitory computer-readable recording medium recording a program, the program causing a computer to execute:

acquiring an endoscopic video captured by an endoscope;

detecting, using a lesion detection model learned in advance, a lesion candidate from the endoscopic video;

generating, using a lesion score estimation model learned in advance, a heat map that represents, for each pixel of an endoscopic image in the endoscopic video, lesion possibilities of the lesion candidate by a color;

extracting, from the heat map, a first threshold area formed by pixels whose lesion possibility, of the lesion possibilities, is equal to or greater than a first threshold, and a second threshold area formed by pixels whose lesion possibility, of the lesion possibilities, is equal to or greater than a second threshold larger than the first threshold;

superimposing and displaying the first threshold area on the endoscopic video in a first display mode and the second threshold area on the endoscopic video in a second display mode, the second display mode having a higher transparency than the first display mode;

superimposing and displaying, inside the second threshold area, a predetermined mark, at any of a center of the second threshold area and a center of gravity of the second threshold area, as a guide to a position of the lesion candidate; and based on a presence of a lesion being determined to be obtained successively a predetermined number of times from the endoscopic video, determine that the lesion candidate is stably detected and include, in display data of the endoscopic image, an indication of a most recent lesion candidate and the heat map as a lesion history.

\* \* \* \* \*